US008506617B1

(12) United States Patent
Michal et al.

(10) Patent No.: US 8,506,617 B1
(45) Date of Patent: Aug. 13, 2013

(54) MICRONIZED PEPTIDE COATED STENT

(75) Inventors: Eugene T Michal, San Francisco, CA (US); Ashok A Shah, San Jose, CA (US); Ni Ding, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2857 days.

(21) Appl. No.: 10/177,942

(22) Filed: Jun. 21, 2002

(51) Int. Cl.
*A61F 2/06* (2006.01)

(52) U.S. Cl.
USPC .......................................... 623/1.15; 424/423

(58) Field of Classification Search
USPC .............. 623/1.15, 1.42, 1.43; 424/423, 484, 424/486
See application file for complete search history.

(56) References Cited

U.S. PATENT DOCUMENTS

| | | | |
|---|---|---|---|
| 2,072,303 A | 3/1937 | Herrmann et al. | 128/335.5 |
| 2,386,454 A | 10/1945 | Frosch et al. | 260/78 |
| 3,773,737 A | 11/1973 | Goodman et al. | 260/78 |
| 3,835,175 A | 9/1974 | Carpino et al. | 260/463 |
| 3,849,514 A | 11/1974 | Gray, Jr. et al. | 260/857 |
| 4,226,243 A | 10/1980 | Shalaby et al. | 128/335.5 |
| 4,329,383 A | 5/1982 | Joh | 428/36 |
| 4,343,931 A | 8/1982 | Barrows | 528/291 |
| 4,529,792 A | 7/1985 | Barrows | 528/291 |
| 4,611,051 A | 9/1986 | Hayes et al. | 528/295.3 |
| 4,656,242 A | 4/1987 | Swan et al. | 528/295.3 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,908,404 A | 3/1990 | Benedict et al. | 525/54.11 |
| 4,917,309 A | 4/1990 | Zander et al. | 241/5 |
| 4,931,287 A | 6/1990 | Bae et al. | 424/484 |
| 4,941,870 A | 7/1990 | Okada et al. | 600/36 |
| 4,977,901 A | 12/1990 | Ofstead | 128/772 |
| 5,019,096 A | 5/1991 | Fox, Jr. et al. | 623/1 |
| 5,025,001 A | 6/1991 | Loscalzo et al. | 514/91 |
| 5,100,992 A | 3/1992 | Cohn et al. | 424/501 |
| 5,112,457 A | 5/1992 | Marchant | 204/165 |
| 5,133,742 A | 7/1992 | Pinchuk | 623/1 |
| 5,155,137 A | 10/1992 | Keefer et al. | 514/611 |
| 5,163,952 A | 11/1992 | Froix | 623/1 |
| 5,165,919 A | 11/1992 | Sasaki et al. | 424/488 |
| 5,187,183 A | 2/1993 | Loscalzo et al. | 514/400 |
| 5,202,129 A | 4/1993 | Samejima et al. | 424/489 |
| 5,219,980 A | 6/1993 | Swidler | 528/272 |
| 5,258,020 A | 11/1993 | Froix | 623/1 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,306,786 A | 4/1994 | Moens et al. | 525/437 |
| 5,328,471 A | 7/1994 | Slepian | 604/101 |
| 5,330,768 A | 7/1994 | Park et al. | 424/501 |
| 5,356,890 A | 10/1994 | Loscalzo et al. | 514/210 |
| 5,366,997 A | 11/1994 | Keefer et al. | 614/611 |
| 5,380,299 A | 1/1995 | Fearnot et al. | 604/265 |
| 5,405,919 A | 4/1995 | Keefer et al. | 525/377 |
| 5,417,981 A | 5/1995 | Endo et al. | 424/486 |
| 5,424,077 A | 6/1995 | Lajoie | 424/641 |
| 5,428,070 A | 6/1995 | Cooke et al. | 514/557 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,482,720 A | 1/1996 | Murphy et al. | 424/489 |
| 5,485,496 A | 1/1996 | Lee et al. | 378/64 |
| 5,516,881 A | 5/1996 | Lee et al. | 528/320 |
| 5,536,723 A | 7/1996 | Loscalzo et al. | 514/247 |
| 5,543,099 A | 8/1996 | Zhang et al. | 264/115 |
| 5,569,463 A | 10/1996 | Helmus et al. | 424/426 |
| 5,578,073 A | 11/1996 | Haimovich et al. | 623/1 |
| 5,584,877 A | 12/1996 | Miyake et al. | 623/1 |
| 5,605,696 A | 2/1997 | Eury et al. | 424/423 |
| 5,607,467 A | 3/1997 | Froix | 623/1 |
| 5,609,629 A | 3/1997 | Fearnot et al. | 623/1 |
| 5,610,241 A | 3/1997 | Lee et al. | 525/411 |
| 5,616,338 A | 4/1997 | Fox, Jr. et al. | 424/423 |
| 5,624,411 A | 4/1997 | Tuch | 604/265 |
| 5,628,730 A | 5/1997 | Shapland et al. | 604/21 |
| 5,639,441 A | 6/1997 | Sievers et al. | 424/9.3 |
| 5,644,020 A | 7/1997 | Timmermann et al. | 528/288 |
| 5,649,977 A | 7/1997 | Campbell | 623/1 |
| 5,650,442 A | 7/1997 | Mitchell et al. | 514/611 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,674,242 A | 10/1997 | Phan et al. | 606/198 |
| 5,679,400 A | 10/1997 | Tuch | 427/2.14 |

(Continued)

FOREIGN PATENT DOCUMENTS

| | | |
|---|---|---|
| DE | 42 24 401 | 1/1994 |
| EP | 0 301 856 | 2/1989 |

(Continued)

OTHER PUBLICATIONS

U.S. Appl. No. 10/177,156, filed Jun. 21, 2002, Michal et al.
U.S. Appl. No. 10/177,116, filed Jun. 21, 2002, Pacetti et al.
U.S. Appl. No. 10/177,114, filed Jun. 21, 2002, Simhambhatla et al.
U.S. Appl. No. 10/176,499, filed Jun. 21, 2002, Hossainy et al.
U.S. Appl. No. 10/176,506, filed Jun. 21, 2002, Claude et al.
U.S. Appl. No. 10/177,117, filed Jun. 21, 2002, Hossainy et al.
U.S. Appl. No. 10/320,899, filed Dec. 16, 2002, Shah et al.
Anonymous, Reducing the pH of a peptide oligomer to prepare for systemic delivery, Defensive Publication, Research Disclosure, p. 905 (Aug. 2003).
Anonymous, *Cardiologists Draw—Up the Dream Stent*, Clinica 710:15 (Jun. 17, 1996), http://www.dialogweb.com/cgi/document?req=1061848202959, printed Aug. 25, 2003 (2 pages).

(Continued)

*Primary Examiner* — Victor Nguyen
(74) *Attorney, Agent, or Firm* — Squire Sanders (US) LLP

(57) ABSTRACT

A coating for an implantable device such as a stent is provided including micronized peptides. A method of making the same is also provided.

33 Claims, No Drawings

(56) References Cited

U.S. PATENT DOCUMENTS

| | | | |
|---|---|---|---|
| 5,700,286 A | 12/1997 | Tartaglia et al. | 623/1 |
| 5,702,754 A | 12/1997 | Zhong | 427/2.12 |
| 5,711,958 A | 1/1998 | Cohn et al. | 424/423 |
| 5,716,981 A | 2/1998 | Hunter et al. | 514/449 |
| 5,721,131 A | 2/1998 | Rudolph et al. | 435/240 |
| 5,723,219 A | 3/1998 | Kolluri et al. | 428/411.1 |
| 5,735,897 A | 4/1998 | Buirge | 623/12 |
| 5,746,998 A | 5/1998 | Torchilin et al. | 424/9.4 |
| 5,759,205 A | 6/1998 | Valentini | 623/16 |
| 5,776,184 A | 7/1998 | Tuch | 623/1 |
| 5,783,657 A | 7/1998 | Pavlin et al. | 528/310 |
| 5,788,979 A | 8/1998 | Alt et al. | 424/426 |
| 5,800,392 A | 9/1998 | Racchini | 604/96 |
| 5,804,318 A | 9/1998 | Pinchuk et al. | 428/421 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,849,859 A | 12/1998 | Acemoglu | 528/271 |
| 5,851,508 A | 12/1998 | Greff et al. | 424/9.411 |
| 5,852,058 A | 12/1998 | Cooke et al. | 514/564 |
| 5,854,376 A | 12/1998 | Higashi | 528/288 |
| 5,858,746 A | 1/1999 | Hubbell et al. | 435/177 |
| 5,861,168 A | 1/1999 | Cooke et al. | 424/424 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,874,165 A | 2/1999 | Drumheller | 428/308.4 |
| 5,876,433 A | 3/1999 | Lunn | 623/1 |
| 5,877,224 A | 3/1999 | Brocchini et al. | 514/772.2 |
| 5,879,713 A | 3/1999 | Roth et al. | 424/489 |
| 5,891,459 A | 4/1999 | Cooke et al. | 424/439 |
| 5,902,875 A | 5/1999 | Roby et al. | 528/310 |
| 5,905,168 A | 5/1999 | Dos Santos et al. | 562/590 |
| 5,910,564 A | 6/1999 | Gruning et al. | 528/310 |
| 5,914,387 A | 6/1999 | Roby et al. | 528/310 |
| 5,919,893 A | 7/1999 | Roby et al. | 525/411 |
| 5,925,720 A | 7/1999 | Kataoka et al. | 525/523 |
| 5,932,299 A | 8/1999 | Katoot | 427/508 |
| 5,945,452 A | 8/1999 | Cooke et al. | 514/564 |
| 5,955,509 A | 9/1999 | Webber et al. | 514/772.7 |
| 5,958,385 A | 9/1999 | Tondeur et al. | 424/61 |
| 5,962,138 A | 10/1999 | Kolluri et al. | 428/411.1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,011,125 A | 1/2000 | Lohmeijer et al. | 525/440 |
| 6,015,541 A | 1/2000 | Greff et al. | 424/1.25 |
| 6,033,582 A | 3/2000 | Lee et al. | 216/37 |
| 6,034,204 A | 3/2000 | Mohr et al. | 528/328 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,054,553 A | 4/2000 | Groth et al. | 528/335 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,060,534 A | 5/2000 | Ronan et al. | 523/113 |
| 6,063,432 A | 5/2000 | Maxwell et al. | 426/656 |
| 6,077,543 A | 6/2000 | Gordon et al. | 424/489 |
| 6,080,488 A | 6/2000 | Hostettler et al. | 428/423.3 |
| 6,095,134 A | 8/2000 | Sievers et al. | 128/200.14 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,117,872 A | 9/2000 | Maxwell et al. | 514/249 |
| 6,120,491 A | 9/2000 | Kohn et al. | 604/502 |
| 6,120,536 A | 9/2000 | Ding et al. | 623/1.43 |
| 6,120,788 A | 9/2000 | Barrows | 424/426 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,136,333 A | 10/2000 | Cohn et al. | 424/423 |
| 6,140,127 A * | 10/2000 | Sprague | 435/395 |
| 6,143,354 A | 11/2000 | Koulik et al. | 427/2.24 |
| 6,153,252 A | 11/2000 | Hossainy et al. | 427/2.3 |
| 6,159,978 A | 12/2000 | Myers et al. | 514/252.1 |
| 6,165,212 A | 12/2000 | Dereume et al. | 623/1.13 |
| 6,172,167 B1 | 1/2001 | Stapert et al. | 525/420 |
| 6,177,523 B1 | 1/2001 | Reich et al. | 525/459 |
| 6,180,632 B1 | 1/2001 | Myers et al. | 514/252.1 |
| 6,183,783 B1 | 2/2001 | Benoit et al. | 424/497 |
| 6,203,551 B1 | 3/2001 | Wu | 606/108 |
| 6,211,249 B1 | 4/2001 | Cohn et al. | 514/772.1 |
| 6,214,901 B1 | 4/2001 | Chudzik et al. | 523/113 |
| 6,228,346 B1 | 5/2001 | Zhang et al. | 424/45 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,258,371 B1 | 7/2001 | Koulik et al. | 424/422 |
| 6,262,034 B1 | 7/2001 | Mathiowitz et al. | 514/44 |
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 4/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 | 10/2001 | Barry et al. | 623/1.46 |
| 6,306,176 B1 | 10/2001 | Whitbourne | 623/23.59 |
| 6,306,993 B1 | 10/2001 | Rothbard et al. | 526/304 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,495,663 B1 * | 12/2002 | Rothbard et al. | 530/329 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,572,894 B2 * | 6/2003 | Rossling et al. | 424/497 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Hossainy et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |

| | | | |
|---|---|---|---|
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,746,481 B1 | 6/2004 | Larik et al. | |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 6,899,898 B2 * | 5/2005 | Albayrak | 424/489 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |
| 2004/0086542 A1 | 5/2004 | Hossainy et al. | 424/423 |
| 2004/0086550 A1 | 5/2004 | Roorda et al. | 424/448 |
| 2004/0096504 A1 | 5/2004 | Michal | 424/471 |
| 2004/0098117 A1 | 5/2004 | Hossainy et al. | 623/1.42 |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |

| WO | WO 00/74701 | 12/2000 |
| WO | WO 01/01890 A1 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 01/74414 | 10/2001 |
| WO | WO 02/03890 | 1/2002 |
| WO | WO 02/26162 | 4/2002 |
| WO | WO 02/34311 | 5/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |

OTHER PUBLICATIONS

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising α-Amino Acid, 1,2-Ethanediol, and Adipic Acid*, Chemistry Letters, pp. 21-24, (1991).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Anderson et al., *Nitric-Oxide and Nitrovasodilators: Similarities, Differences and Potential Interactions*, JACC 24(2):555-566 (1994).

Anderson et al., *Close Relation of Endothelial Function in the Human Coronary and Peripheral Circulations*, JACC 26(5):1235-1241 (1995).

Bode-Boger et al., *Elevated L-Arginine/Dimethylarginine Ratio Contributes to Enhanced Systemic NO Production by Dietary L-Arginine in Hypercholesterolemic Rabbits*, Biochem. and Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al, *Asymmetric Dimethylarginine: A Novel Risk Factor for Endothelial Dysfunction*, Circ. 96(8):I-32 (1997).

Boger et al., *The Endogenous NO Synthase Inhibitor Asymmetric Dimethyl-L-Arginine (ADMA) Regulates Endothelial NO Production and Adhesiveness for Monocytes (Abstract J5)*, Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).
Candipan et al., *Regression or Progression: Dependency on Vascular Nitric Oxide*, Arterioscler. Thromb. Vasc. Biol. 16(1):44-50 (1996).
Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).
Cooke et al., *Arginine: A New Therapy for Atherosclerosis?* Circ. 95(2):311-312 (1997).
Cooke et al., *Cytoprotective Effects of Nitric Oxide*, Circ. 88(5)1:2451-2454 (1993).
Cooke et al., *Derangements of the Nitric Oxide Synthase Pathway, L-Arginine, and Cardiovascular Diseases*, Circ. 96(2):379-382 (1997).
Cooke et al., *Diffuse Coronary Artery Disease and Endothelial Dysfunction: Form Follows Function*, ACC Curr. J. Rev. pp. 19-25 (Nov./Dec. 2000).
Cooke et al., *Regression and Progression: Dependency Upon NO* (Abstract), J. Investi. Med. 43(2) Suppl. 2:211A (1995).
Cooke et al., *The Role of Endothelium-Derived Nitric Oxide in Atherosclerosis*, Adv. Vasc. Path. 1150:3-14 (1997).
Cooke, *Does ADMA Cause Endothelial Dysfunction?*, Arterioscler. Thromb. Vasc. Biol. 20:2032-2037 (2002).
Cooke, *Enhancement of Endogenous Vascular Nitric Oxide: A New Therapeutic Strategy for Restenosis* (Abstract 301), Eur. J. Clin. Invest 28:A53 (1998).
Cooke, *Is Atherosclerosis an Arginine Deficiency Disease?*, J. Investi. Med. 46(8):377-380 (1998).
Cooke, *Nutriceuticals for Cardiovascular Health*, Am. J. Cardio., 82(10A):43S-46S (1998).
Cooke, *Role of Nitric Oxide in Progression and Regression of Atherosclerosis*, West. J. Med. 164(5):419-424 (1996).
Cooke, *The 1998 Nobel Prize in Medicine: Clinical Implications for 1999 and Beyond*, Vasc. Med. 4:57-60 (1999).
Cooke, *The Endothelium: A New Target for Therapy*, Vasc. Med. 5:49-43 (2000).
Cooke, *The Pathophysiology of Peripheral Arterial Disease: Rational Targets for Drug Intervention*, Vasc. Med. 2:227-230 (1997).
Creager et al, *L-Arginine Improves Endothelium-Dependent Vasodilation in Hypercholesterolemic Humans*, J. Clin. Investi. 90:1248-1253 (1992).
Drexler et al., *Effect of L-Arginine on Coronary Endothelial Function in Cardiac Transplant Recipients: Relation to Vessel Wall Morphology*, Circ. 89(4):1615-1623 (1994).
Drexler et al., *Endothelial Dysfunction in the Coronary Circulation After Cardiac Transplantation: Effect of L-Arginine* (Abstract 1356), Circ. 86(4) Supp:1418(1992).
Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).
http://www.lf2.cuni.dz/physiolres/1997/issue5/iss5c16.html,
Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).
Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).
Ganz et al., *Coronary Vasospasm in Humans—The Role of Atherosclerosis and of Impaired Endothelial Vasodilator Function*, Basic Res. Cardiol. 86(Suppl 2):215-222 (1991).
Gregory et al., *Enhanced Nitric Oxide Production Induced by the Administration of L-Arginine Does Not Inhibit Arterial Neointimal Formation After Overwhelming Alloimmune Injury*, J. Heart Lung Transplant. 15(1)Part 1:58-66 (1996).
Gregory et al., *Nitric Oxide Induced by the Administration of L-Arginine Does Not Inhibit Aterial Neointimal Formation Following Alloimmune Injury* (Abstract 41), J. Heart Lung Transplant. 14(1)Part 2:S45 (1995).
Heeschen et al., *Hypercholesterolemia Impairs Angiogenic Response to Hind Limb Ischemia*: Role of ADMA (Abstract 2490), Circ. I-473 (1999).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).
Huet et al., *Structural Homologies Between Two HLA B27-Restricted Peptides Suggest Residues Important for Interaction with HLA B27*, Intl. Immunol. 2(4):311-316 (1990).
Hutchison et al., *Effects of L-Arginine on Atherogenesis and Endothelial Dysfunction Due to Secondhand Smoke*, Hyperten. 34:44-50 (1999).
Jang et al., *Angiogenesis is Impaired by Hypercholesterolemia: Role of Asymmetric Dimethylarginine*, Circ. 102:1414-1419 (2000).
Jang et al., *L-Arginine Reverses the Anti-Angiogenic Effects of Asymmetric Dimethylarginine* (Abstract), J. Investi. Med. 4(2):86A (1999).
Jozkowicz et al., *Genetic Augmentation of Nitric Oxide Synthase Increases the Vascular Generation of VEGF*, Cardiovasc. Res. 51:773-783 (2001).
Kown et al., *Arginine Polymers Inhibit Graft Coronary Artery Disease Following Cardiac Transplantation* (Abstract 726), Transplant. 69(8):S300 (2000).
Kown et al., *L-Arginine Polymers Inhibit the Development of Vein Graft Neointimal Hyperplasia*, J. Thorac. Cardiovasc. Surg. 121(5):971-980 (2001).
Kown et al., *L-Arginine Polymer Mediated Inhibition of Graft Coronary Artery Disease After Cardiac Transplantation*, Transplant. 71(11):1542-1548 (2001).
Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).
Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).
Kyte et al., *A Simple Method for Displaying the Hydropathic Character of a Protein*, J. Mol. Biol. 157:105-132 (1982).
Latron et al., *Positioning of a Peptide in the Cleft of HLA-A2 by Complementing Amino Acid Changes*, PNAS 88:11325-11329 (1991).
Lieberman et al., *Estrogen Improves Endothelium-Dependent, Flow-Mediated Vasodilation in Postmenopausal Women*, Annals Intern. Med. 121(12):936-941 (1994).
Lieberman et al., *Flow-Induced Vasodilation of the Human Brachial Artery is Impaired in Patients <40 Years of Age with Coronary Artery Disease*, Am. J. Cardiol. 78:1210-1214 (1996).
Lim et al., *Acute Local Delivery of L-Arginine Reduces Long Term Intimal Thickening and Macrophage Infiltration* (Abstract 2346), Circ. 94(8):I403 (1996).
Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).
Lissin et al., *Maintaining the Endothelium: Preventive Strategies for Vessel Integrity*, Prev. Cardio. 3:172-177 (2000).
Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).
Maxwell et al., *A Nutritional Product Designed to Enhance Nitric Oxide Activity Restores Endothelium-Dependent Function in Hypercholesterolemia*, J. Investi. Med. 47(2):45A (1999).
Maxwell et al., *Cardiovascular Effects of L-Arginine*, Curr. Opin. Nephrol. Hyperten. 7:63-70 (1998).
Maxwell et al., *Endothelial Dysfunction in Hypercholesterolemia is Reversed by a Nutritional Product Designed to Enhance Nitric Oxide Activity*, Cardiovasc. Drugs Therapy 14:309-316 (2000).
Maxwell et al., *Improvement in Walking Distance and Quality of Life in Peripheral Arterial Disease by a Medical Food* (Abstract 86), Nitric Oxide: Biology and Chemistry, 4(3):232 (2000).
Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercise Capacity in Association with Augmented Nitric Oxide Production*, J. Appl. Physiol. 90:933-938 (2001).

Maxwell et al., *Limb Blood Flow During Exercise is Dependent on Nitric Oxide*, Circ. 98:369-374 (1998).

Maxwell et al., *Modulation of the Nitric Oxide Synthase Pathway in Atherosclerosis*, Exp. Physiol. 83:573-584 (1998).

Maxwell et al., *Nutritional Therapy for Peripheral Arterial Disease: A Double-Blind, Placebo-Controlled, Randomized Trial of HeartBar®*, Vasc. Med. 5:11-19 (2000).

Maxwell et al., *The Role of Nitric Oxide in Atherosclerosis*, Cor. Art. Dis. 10:277-286 (1999).

Meredith et al., *Role of Endothelium in Ischemic Coronary Syndromes*, Am. J. Cardiol. 72(8):27C-32C (1993).

Meredith et al., *Role of Impaired Endothelium-Dependent Vasodilation in Ischemic Manifestations of Coronary Artery Disease*, Circ. 87(5) Suppl:V56-V66 (1993).

Mitchell et al.; *Polyarginine Enters Cells More Efficiently than Other Polycationic Homopolymers*, J. Peptide Res. 56:318-325 (2000).

Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate in the Absence of Changes in Arterial Blood Pressure When Applied Topically to the Sino-Atrial Node in the Anaesthetized Pig*, J. Physiol. (2000), printed Jun. 12, 2001.

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:1-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone in vivo Using Intravascular Ultrasound*, J. Pharmacol, Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity in vivo*, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7 (1):14-17 (2000).

Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester*, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract 120), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Alter Vascular Reactivity in Hypercholesterolemic Animals* (Abstract) Clin. Res. 41(1):78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and the Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by the NO Precursor* (Abstract 765-4), JACC 25:276A (1995).

Todd et al., *Regulation of Loblolly Pine (Pinus taedaL.) Arginase in Developing Seedling Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion: in vivo Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase as an in vivo Gene Transfer Approach to Prevent Neointima Formation After Vascular Injury*, Clin. Res. 42(2):180A (1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine in Cardiovascular Health*, U.S. Pharmacist Continuing Education, printed Sep. 12, 2002.

* cited by examiner

MICRONIZED PEPTIDE COATED STENT

BACKGROUND OF THE INVENTION

1. Field of the Invention

This invention relates to coatings for implantable devices, such as stents, containing a micronized peptide.

2. Description of the Background

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location.

Stents are used not only for mechanical intervention but also as vehicles for providing biological therapy. Biological therapy can be achieved by medicating the stents. Medicated stents provide for the local administration of an active agent at the diseased site. Local delivery of an active agent is a preferred method of treatment because the agent is concentrated at a specific site and thus smaller total levels of One method of medicating a stent involves the use of a polymeric carrier coated onto the surface of the stent. A composition including a solvent, a polymer dissolved in the solvent, and an active agent dispersed in the blend is applied to the stent by immersing the stent in the composition or by spraying the composition onto the stent. The solvent is allowed to evaporate, leaving on the stent surfaces a coating of the polymer and the active agent impregnated in the polymer.

A potential problem with the above-described method of medicating a stent is that there can be solvent incompatibility among the components of the composition. For example, if the various components are combined to form a composition, and one of the components is immiscible in the solvent of the composition, the immiscible component will form an agglomeration. If the active agent is insoluble in the solvent used for the composition, for instance, the active agent can form crystalline masses in the wet coating and will remain clumped together in the dry coating. When the coated stent is immersed in the aqueous environment of the body, the active agent will quickly disperse into the blood stream. This result is undesirable in many circumstances because therapeutic treatment often requires a prolonged and sustained release of the active agent from the coating matrix.

In view of the foregoing, it is desirable to achieve a process that allows components with incompatible solubility profiles to be combined in a composition used to coat stents. For example, it is desirable to achieve a process that allows polycationic peptides to be combined with hydrophobic polymers. The present invention addresses such problems by providing a coating for implantable devices, and a method of making the coating.

SUMMARY OF THE INVENTION

In accordance with one aspect of the invention, a stent used for implantation at a selected region of a vessel is disclosed including a coating having a polymer and a micronized peptide, such as a peptide having from 5 to 20 L-arginine subunits, or analogs or derivatives thereof, contained in the polymer for the release of the peptide subsequent to the implantation of the stent. In one embodiment, the peptide has an average particle size of less than 2 microns. In another embodiment, the solubility profile of the peptide is incompatible with the solubility profile of the polymer.

In accordance with another aspect of the invention, a method of coating a stent is disclosed including applying a composition to a stent, the composition including a micronized peptide and a fluid, and essentially removing the fluid from the composition on the stent to form a coating. The micronized peptide can be a peptide consisting of from 5 to 20 L-arginine subunits, or analogs or derivatives thereof. In one embodiment, the peptide is micronized by a process including providing a solution containing the peptide, atomizing the solution to produce an aerosol and directing the aerosol into a supercritical fluid to produce micronized particles. In another embodiment, the peptide is micronized by a process including providing a solution containing the peptide, atomizing the solution to produce an aerosol and directing the aerosol into a liquid gas to produce micronized particles.

DETAILED DESCRIPTION

For ease of discussion, the coatings and methods detailed herein will be described with reference to a coating for a stent, e.g., self-expandable or balloon expandable type. However, the device or prosthesis coated in accordance with embodiments of the present invention may be any suitable medical substrate that can be implanted in a human or veterinary patient. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Method of Coating a Stent

In an embodiment of the present invention, a method of coating a stent is provided, including combining a micronized active agent with a polymer and a solvent to form a composition, applying the composition to a stent, and removing the solvent from the composition on the stent to form a coating. By using active agent particles with reduced sizes, this method can be used to combine an active agent with a polymer to form a coating composition even though the active agent has a solubility profile that is not compatible with the solubility profile of the polymer. In other words, the method can be used to combine the active agent with a polymer even though the active agent is immiscible in the solvents that dissolve the polymer.

In a particular example, it has been difficult to incorporate L-arginine or its oligomers into a conventional polymer coating. L-arginine, commonly abbreviated as "R" or "Arg," also known as 2-amino-5-guanidinovaleric acid, has a formula $NH=C(NH_2)-NH-(CH_2)_3-CH(NH_2)-COOH$. L-arginine is an amino acid. Due to the presence of a strong basic guanidinium group, —NH—C(NH$_2$)=NH, carrying a partially uncompensated positive charge, L-arginine, and its polymers and/or oligomers are highly cationic. For example, the heptamer of L-arginine has a pK$_a$ of 13.2.

Polymers and/or oligomers of L-arginine that can be used are referred to herein as "PArg." PArg are polycationic peptides comprising a plurality of repeating monomeric amino acid units and have a general formula H—[NH—CHX—CO]$_p$—OH, where "p" can be within a range of 5 and 1,000, typically, within a range of between 5 and 20. For example, a heptamer (designated R7) or a nonamer (R9), having p=7 and p=9, respectively, can be used. In the formula of PArg, "X" is 1-guanidinopropyl radical having the structure —CH$_2$—CH$_2$—CH$_2$—NH—C(NH$_2$)=NH. The terms "polymers and/or oligomers of L-arginine" and "PArg" are intended to include L-arginine in both its polymeric and oligomeric form.

In addition to PArg, other polycationic peptides can be alternatively used. Examples of such alternative polycationic peptides include poly(L-arginine), poly(D-arginine), poly(L-lysine), poly(D-lysine), poly(δ-guanidino-α-aminobutyric acid), racemic mixtures of poly(L-arginine) and poly(D-arginine), and chitosan.

As discussed above, L-arginine is highly cationic due to the strong basicity of the guanidinium group of L-arginine. This high degree of polarity causes L-arginine and its polymers and/or oligomers to be generally insoluble in most organic solvents, leaving water as one of the few solvent alternatives. However, most coating polymers (e.g., ethylene vinyl alcohol copolymer) are soluble in organic solvents, but not in water. Accordingly, the solvent profile of PArg is incompatible with many polymers, and therefore it is difficult to incorporate PArg into stent coatings using conventional coating techniques. By using particles of PArg with reduced sizes, the method of the present invention can be used to combine PArg with a polymer to form a coating composition even though the PArg has a solubility profile that is not compatible with the solubility profile of the polymer.

"Micronized" refers to particles that have been reduced in size to only a few microns in diameter, or a solution which has been atomized so that the liquid droplets of the solution are only a few microns in diameter.

"Organic solvent" refers to an organic solvent or a solvent mixture having at least one organic component. The solvent mixture can also include mixtures of water with miscible organic solvents.

"Solubility profile" refers to the general solubility characteristics of a particular compound or mixture of compounds including the solvents that can be used to dissolve the compound or mixture of compounds, and the physical variables such as pH and temperature that can be used to increase or decrease the solubility of the compound or mixture of compounds.

"Hydrophilic" refers to a component is that is water-soluble, or has an affinity for absorbing water (e.g., a hydrogel polymer) or tends to combine with water.

"Water-soluble" refers to components which have a greater solubility in water than in organic solvents and are commonly highly soluble in water. Although certain regions or segments of the component may be hydrophobic, the component as a whole is capable of substantially dissolving in water or aqueous-based systems, or a highly polar solvent(s). Typical aqueous solubilities of hydrophilic components at 20° C. will be equal to or greater than 5 mg/ml, usually greater than 50 mg/ml, and often greater than 100 mg/ml.

"Hydrophobic" refers to a component that is water-insoluble, or does not have an affinity for absorbing water or does not tend to combine with water.

"Water-insoluble" refers to components which have a greater solubility in organic solvents than in water and are commonly insoluble or poorly soluble in water. Although certain regions or segments of the component may be hydrophilic, the component as a whole is capable of substantially dissolving in organic solvents. Typically, the solubility for such components in water at 20° C. will be below 5 mg/ml, usually below 1 mg/ml.

Once the micronized active agent has been combined with the polymer and the solvent to form a composition, the composition can be applied to a stent by any conventional method, such as by spraying the composition onto the device or immersing the device in the composition. The stent can optionally be partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "web" formation between the stent struts.

Operations such as wiping, centrifugation, or other web clearing acts can be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

After the composition is applied to the stent, the solvent is removed from the composition on the stent by allowing the solvent to evaporate. The evaporation can be induced by heating the stent at a predetermined temperature for a predetermined period of time. For example, the stent can be heated at a temperature of about 80° C. for about 1 hour to about 24 hours. The heating can be conducted under a vacuum condition. It is understood that essentially all of the solvent will be removed from the composition but traces or residues can remain blended with the other ingredients.

The particular thickness of the coating is based on the type of procedure for which the stent is employed and the amount of active agents that is desired to be delivered. By way of example and not limitation, the coating can have a thickness of 2 microns to about 15 microns. Applying a plurality of reservoir coating layers, containing the same or different active agent, onto the stent can further increase the amount of the active agent to be carried by the stent.

Methods of Micronizing the Active Agent

Before the active agent is combined with the polymer and solvent, the active agent should be micronized to reduce the size of active agent particles. For example, particles of active agent can be micronized by wet milling or dry milling. Additionally, a solution of the active agent can be atomized to produce an aerosol, and the aerosol can be directed into a supercritical fluid or a liquid gas in order to produce micronized particles. In one embodiment, the average particle size is less than 2 microns.

"Particle" refers to solid particles. "Average particle size" refers to the average of the largest dimension of the particles. Preferably, the size distribution of the particle sizes will be substantially uniform. For example, the micronized active agent will have particles with a size distribution where a substantial majority (e.g., at least 90%) of the particles have a particle size less than about 2 microns. Additionally, it is preferred that the particle size distribution does not have an excess amount of particles with very small particle sizes (e.g., less than 0.3 microns). The average particle size can be determined by a number of conventional particle size analyzers such as a LA-300 Particle Size Analyzer (Horiba Laboratory Products, Irvine, Calif.).

Dry Milling

Several different types of mills can be used to micronize the active agents. For example, some dry mills are capable of grinding the active agent into ultrafine particles through mechanical impact and/or attrition, such as high-speed stirring mills and impact mills. Representative examples of dry mills are cylinder-type mills such as a rotating ball mill, vibrating ball mills, and hammer mills. A particle size analyzer can be used during the micronization process to ensure that the active agent particles are being ground to the desired average particle size.

Another representative example of a dry mill for the present process is a jet mill which is a size reduction machine in which particles to be ground are accelerated in a stream of gas, (e.g., compressed air) and micronized in a grinding chamber by their impact against each other or against a stationary surface in the grinding chamber. Different types of jet mills can be categorized by their particular mode of operation. Jet mills, for instance, may be distinguished by the location of feed particles with respect to incoming air. Micronization can be performed by any number of commercially available jet mills such as the Micron-Master® (The Jet Pulverizer Company, Moorestown, N.J.). The Micron-Master® is a continuous operating pulverizer with capacities of ½ to 4000 lbs/hr and can grind crystalline or friable materials, in a dry state, finely and uniformly to an average particle size of about 0.25 microns to about 5 microns. In addition, the Micron-Master® can produce a substantially uniform homogeneous random blend of micronized particles from a mix of two or more active agents.

Wet Milling

The active agent can also be micronized by conventional wet milling techniques. Wet milling techniques utilize an aqueous solution or an organic solvent during the process, and can use mills similar to those used in dry milling techniques. Suitable mills for wet milling can include hammer mills, impact mills (where particle size reduction/control is achieved by impact of the active agent particles with metal blades and retained by an appropriately sized screen), and sand mills (where particle size control/reduction is achieved by contact of the active agent with hard media such as sand or zirconia beads). Another type of conventional wet milling equipment that can be used for the procedure includes an ultrasonic homogenizer (Cole-Parmer Instrument Company, Vernon Hills, Ill.). As an example, a wet milling procedure can be carried out in an aluminum vessel filled with 3 mm-zirconia grinding balls (YTZ® grinding media, Tosoh Co., Japan), and a polymer and organic solvent.

The wet milling procedure can also be used in addition to the dry milling procedure. For example, a previously dry, milled, active agent can be subjected to a wet milling that will result in a further reduction of the average particle size initially imparted by the dry milling procedure.

Exposure to Liquid Gasses

The active agent can also be micronized by exposing the active agent to a liquid gas. In particular, the active agent can be dissolved in solution, and atomized to produce an aerosol by a conventional spraying apparatus. The aerosol can then be directed into a liquid gas which quickly freezes the liquid droplets of active agent solution to form solid particles. Because the liquid droplets are quickly frozen, the droplets do not have sufficient time to aggregate into larger droplets.

Representative examples of liquid gasses that can be used include nitrogen, argon, helium, hydrogen and oxygen.

If the active agent is initially dissolved in an aqueous solution, after the droplets are frozen, the water in the particles can be removed. For instance, frozen active agent particles can be freeze-dried by using conventional methods, or the water from the active agent particles can be extracted by water miscible solvents such as acetone or tetrahydrofuran.

Depending on the process parameters and the chemical characteristics of the active agent (e.g., peptide) and other components of the composition, the active agent may not be stable in solution. Therefore, it may be necessary to add a stabilizer to the active agent solution such as a surfactant (e.g., sodium dodecyl sulfate), a carbohydrate (e.g., a polysaccharide such as heparin), or a water-soluble salt such as sodium chloride.

Exposure to Supercritical Fluids

The active agent particles can be micronized by a process that utilizes supercritical fluids. Typically this process includes first dissolving an active agent in an aqueous solution, which is then mixed under pressure with a supercritical fluid to form an emulsion. Next, the mixture is directed through a nebulizer which atomizes the mixture through rapid decompression to form an aerosol of frozen particles. The micronized particles are then directed through a drying chamber in order to remove the water from the particles, after which the particles are collected. The foregoing process can be performed by using conventional micronizing equipment, such as the Temco Instruments Model BD-200 Bubble Dryer™ (Temco Instruments, Tulsa, Okla.).

As used herein the term "supercritical fluid" should be considered to encompass near-supercritical fluids, i.e., highly compressed fluids that are below the critical temperature point, yet exhibit many of the same qualities of true supercritical fluids, such as high solvating power and compressibility. Representative examples of supercritical fluids include carbon dioxide, sulfur hexafluoride, chlorofluorocarbons, fluorocarbons, nitrous oxide, xenon, propane, n-pentane, ethanol, nitrogen, and water. Depending on the active agent, the solubility of the supercritical fluid may be less than is desirable, and therefore the supercritical fluids can be a mixture of the foregoing in order to increase the solubility. In one preferred embodiment, the supercritical fluid is carbon dioxide or mixtures of carbon dioxide with another gas such as fluoroform or ethanol. Carbon dioxide has a critical temperature of 31.3° C. and a critical pressure of 72.9 atmospheres (1072 psi), low chemical reactivity, physiological safety, and is relatively inexpensive.

During this process, depending on the process parameters and the chemical characteristics of the active agent (e.g., peptide) and other components of the composition, the active agent may not be stable in solution. Therefore, it may be necessary to add a stabilizer to the active agent solution such as a surfactant (e.g., sodium dodecyl sulfate), a carbohydrate (e.g., a polysaccharide such as heparin), or a water-soluble salt such as sodium chloride.

Embodiments of the Composition

The composition used to form the coating for the stent can include a solvent, a polymer dissolved in the solvent, and an active agent. Representative examples of polymers that can be used to coat a stent in accordance with the present invention include ethylene vinyl alcohol copolymer (commonly known by the generic name EVOH or by the trade name EVAL); polybutylmethacrylate; poly(hydroxyvalerate); poly (L-lactic acid); polycaprolactone; poly(lactide-co-glycolide); poly(hydroxybutyrate); poly(hydroxybutyrate-co-valerate); polydioxanone; styrene-ethylene/propylene-styrene polymers (KRATON G series, available from Kraton Polymers, Houston, Tex.); polyorthoester; polyanhydride; poly(glycolic acid); poly(D,L-lactic acid); poly(glycolic acid-co-trimethylene carbonate); polyphosphoester; polyphosphoester urethane; poly(trimethylene carbonate); poly (iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; polyisocyanate; polyethylene glycol; polyvinyl pyrrolidone; poly(2-hydroxyethyl methacrylate); polyacrylic acid; epoxy resins; polyurethanes; rayon; rayon-triacetate; cellulose acetate; cellulose butyrate; cellulose acetate butyrate; cellophane; cellulose nitrate; cellulose propionate; cellulose ethers; and carboxymethyl cellulose.

In accordance with an embodiment of the invention, a hydrophobic component (e.g., polymer) is dissolved in an organic solvent. "Solvent" refers to a liquid substance or composition that is compatible with the target component and is capable of dissolving the component at the concentration desired in the composition. A representative example of a solvent for hydrophilic components includes water. Representative examples of solvents for hydrophobic components include chloroform, acetone, dimethylsulfoxide, propylene glycol methyl ether, iso-propylalcohol, tetrahydrofuran, dimethylformamide, dimethyl acetamide, benzene, toluene, xylene, hexane, cyclohexane, heptane, octane, nonane, decane, decalin, ethyl acetate, butyl acetate, cyclohexanone, cyclohexanol, 1,4-dioxane, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloroethane, chlorobenzene, 1,1,1-trichloroethane, formamide, hexafluoroisopropanol, 1,1,1-trifluoroethanol, and hexamethyl phosphoramide, and a combination thereof.

In an embodiment of the present invention, a micronized active agent is added to a polymer and a solvent to form a composition for a stent coating. In another embodiment, a second active agent that has not been micronized can also be added to the composition. The active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the active agent can be for enhancing wound healing in a vascular site or improving the structural and elastic properties of the vascular site.

An example of a suitable group of active agents includes hydrophilic peptides, including oligopeptides and polypeptides, and proteins. For instance, the hydrophilic peptide could be a peptide having from 5 to 20 L-arginine subunits, or functional analogs or structural derivatives thereof. In a more particular example, the peptide can usefully be heptaarginine (R7). L-arginine and its oligomers are known to be therapeutically beneficial substances. One beneficial property of L-arginine and its oligomers is that L-arginine is known to be a precursor of endothelium derived nitric oxide (NO). NO is synthesized from L-arginine and its oligomers by the enzyme NO synthase, a homodimeric flavo-hemoprotein that catalyzes the 5-electron oxidation of L-arginine to produce NO and L-citrulline. Among other therapeutic properties, NO relaxes vascular smooth muscle and inhibits its proliferation.

"Peptide" refers to a compound made up of a single chain of D- or L-amino acids or a mixture of D- and L-amino acids joined by peptide bonds.

"Oligopeptide" refers to a peptide composed of less than 50 amino acid residues.

"Polypeptide" refers to a peptide composed of at least 50 amino acid residues.

"Protein" refers to a macromolecule composed of one or more polypeptide chains with one or more characteristic conformations.

Representative examples of other active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax® (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is pemirolast potassium. Other therapeutic substances or agents which may be appropriate include alpha-interferon, genetically engineered epithelial cells, retinoic acid, suramin, asiaticoside, hyaluronan, heparin sulfate, heparin having a hydrophobic counterion, mannose-6-phosphate, superoxide dismutase rapamycin, rapamycin analogs and derivatives, and dexamethasone. The foregoing substances are listed by way of example and are not meant to be limiting. Other active agents which are currently available or that may be developed in the future are equally applicable.

The dosage or concentration of the active agent required to produce a favorable therapeutic effect should be less than the level at which the active agent produces toxic effects and greater than the level at which non-therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Preparation of the Composition

The composition can be prepared by conventional methods wherein all components are combined, then blended. More particularly, a predetermined amount of a polymer can be added to a predetermined amount of a solvent or a combination of solvents. The mixture can be prepared in ambient pressure and under anhydrous atmosphere. Heating and stirring and/or mixing can be employed to effect dissolution of the polymer into the solvent.

Next, sufficient amounts of a micronized active agent is dispersed in the blended mixture of the polymer and the solvent. "Dispersed" refers to the particles being substantially present as individual particles, not agglomerates or flocs. In certain polymer-solvent blends, certain micronized active agents will disperse with ordinary mixing. Otherwise the micronized active agent can be dispersed in the composition by high shear processes such as using a rotor stator mixer or ultrasonication, which are well known to one of ordinary skill in the art. Biocompatible dispersing agents in the form of surfactants, emulsifiers, or stabilizers may also be added to the blend to assist in particle dispersion.

If a second active agent is added to the composition, and is not micronized, the second active agent is usefully put into solution in the blended composition. If the active agent is not completely soluble in the composition, operations including mixing, stirring, and/or agitation can be employed to effect homogeneity of the residues. The mixing of the active agent can be conducted in an anhydrous atmosphere, at ambient pressure, and at room temperature.

It should be noted that although the methods of the present invention are particularly useful for forming pharmaceutical compositions where the hydrophilic component is a hydrophilic active agent and the hydrophobic component is a hydrophobic polymer, the methods may be applied more broadly to form compositions including hydrophobic active agents and hydrophilic polymers.

Optional Coating Layers

In one embodiment, an optional primer layer can be formed prior to the reservoir coating. "Reservoir coating" refers to the coating which includes an active agent. The primer can increase the retention of the reservoir coating on the surface of the stent, particularly metallic surfaces such as stainless steel. The primer layer can act as an intermediary adhesive tie layer between the surface of the device and a reservoir coating, allowing for the quantity of the active agent to be increased in the reservoir coating. To form an optional primer layer on the surface of the stent, a composition that is free from active agents is applied to the surface of the stent.

A representative example of a polymer to be used as a primer layer is ethylene vinyl alcohol copolymer which adheres very well to metallic surfaces, particularly stainless steel. Accordingly, the copolymer provides for a strong adhesive tie between the reservoir coating and the surface of the implantable device. Another representative example of a polymer that can be used in a primer layer is polybutylmethacrylate.

With the use of thermoplastic polymers such as, but not limited to, ethylene vinyl alcohol copolymer, polycaprolactone, poly(lactide-co-glycolide), and poly(hydroxybutyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of the implantable device. The device should be exposed to the heat treatment for any suitable duration of time that will allow for the formation of the primer layer on the surface of the implantable device and for the evaporation of the solvent employed. By way of example and not limitation, the optional primer layer can have a thickness of about 0.01 microns to about 1 micron. The application of the reservoir coating should be performed subsequent to the drying of the optional primer layer.

In another embodiment, an optional diffusion barrier can be formed over a reservoir coating to reduce the rate at which the active agent is released from the coated stent. A composition, free from any active agents, can be applied to a selected portion of the reservoir coating subsequent to the drying of the reservoir coating. The diffusion barrier may be composed of a different polymer from that used in the reservoir coating or the same material. The diffusion barrier can have a thickness of about 0.2 microns to about 10 microns. It is understood by one of ordinary skill in the art that the thickness of the diffusion barrier is based on factors such as the type of stent, the type of procedure for which the stent is employed, and the rate of release that is desired.

Method of Use

In accordance with embodiments of the above-described method, an active agent can be applied to an implantable device or prosthesis, e.g., a stent, retained on the stent during delivery and expansion of the stent, and released at a desired rate and for a predetermined duration of time at the site of implantation. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

Briefly, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

EXAMPLES

The embodiments of the present invention will be illustrated by the following set forth examples. All parameters and data are not to be construed to unduly limit the scope of the embodiments of the invention.

Example 1

0.4 grams of dry heptaarginine (R7) is combined with 0.4 grams of polybutylmethacrylate (PBMA) and 4 grams of toluene in a cylindrical, 20 cm$^3$ stainless steel mill. 10 cm$^3$ of 1 mm zirconia beads (YTZ® grinding media, Tosoh Co., Japan) are added to the mill. The mill is sealed and shaken to reduce the size of the R7 particles. During the process, the average particle size of the R7 particles is monitored by using a LA-300 Particle Size Analyzer (Horiba Laboratory Products, Irvine, Calif.). After the R7 particles have been reduced to the desired average particle size, a solution of 0.8 grams of PBMA and 8 grams of toluene is added to the mill, and the mill is additionally shaken to homogenize the mixture. The mixture is then poured through a 0.3 mm sieve to remove the zirconia beads. For spray application, the viscosity of the mixture can be further reduced by adding toluene. The composition that results from the foregoing process can then be applied to a stent by using an EFD 780S spray coater (manufactured by EFD Inc., East Providence, R.I.).

Example 2

0.4 grams of dry R7 is combined with 0.4 grams of cellulose acetate butyrate (CAB), 3.2 grams of toluene and 0.8 gram of isoproponol alcohol (IPA) in a cylindrical, 20 cm$^3$ stainless steel mill. 10 cm$^3$ of 1 mm zirconia beads (YTZ® grinding media) are added to the mill. The mill is sealed and shaken to reduce the size of the R7 particles. During the process, the average particle size of the R7 particles is monitored by using a LA-300 Particle Size Analyzer. After the R7 particles have been reduced to the desired average particle size, a solution of 0.8 grams of CAB, 6.4 grams of toluene and 1.6 grams of IPA is added to the mill, and the mill is additionally shaken to homogenize the mixture. The mixture is then poured through a 0.3 mm sieve to remove the zirconia beads. For spray application, the viscosity of the mixture can be further reduced by adding toluene. The composition that results from the foregoing process can then be applied to a stent by using an EFD 780S spray coater.

Example 3

0.4 grams of dry R7 is combined with 0.2 grams of ethylene vinyl alcohol copolymer (EVAL) and 4 grams of dimethyl acetamide (DMAC) in a cylindrical, 20 cm$^3$ stainless steel mill. 10 cm$^3$ of 1 mm zirconia beads (YTZ® grinding media) are added to the mill. The mill is sealed and shaken to reduce the size of the R7 particles. During the process, the average particle size of the R7 particles is monitored by using a LA-300 Particle Size Analyzer. After the R7 particles have been reduced to the desired average particle size, a solution of 0.4 grams of EVAL and 8 grams of DMAC is added to the mill, and the mill is additionally shaken to homogenize the mixture. The mixture is then poured through a 0.3 mm sieve to remove the zirconia beads. For spray application, the viscosity of the mixture can be further reduced by adding DMAC. The composition that results from the foregoing process can then be applied to a stent by using an EFD 780S spray coater.

Example 4

0.4 grams of dry R7 is combined with 0.4 grams of PBMA and 4 grams of toluene in a cylindrical, 20 cm$^3$ stainless steel mill. A probe from an ultrasonic homogenizer (Cole-Parmer Instrument Company, Vernon Hills, Ill.) is inserted into the mill and activated to reduce the size of the R7 particles. During the process, the average particle size of the R7 particles is monitored by using a LA-300 Particle Size Analyzer. After the R7 particles have been reduced to the desired average particle size of less than 2 microns, a solution of 0.8 grams of PBMA and 8 grams of toluene is added to the mill, and the mill is additionally shaken to homogenize the mixture. The mixture is then poured through a 0.3 mm sieve to remove the zirconia beads. For spray application, the viscosity of the mixture can be further reduced by adding toluene. The composition that results from the foregoing process can then be applied to a stent by using an EFD 780S spray coater.

Example 5

Dry R7 is placed in a Micron-Master® jet mill and the mill is activated. During the process, the average particle size of the R7 particles is monitored by using a LA-300 Particle Size Analyzer. After the R7 particles have been reduced to the desired average particle size, the R7 particles are dispersed in a solution of 1.2 grams of PBMA and 36 grams of toluene. The composition that results from the foregoing process can then be applied to a stent by using an EFD 780S spray coater.

Example 6

0.5 grams of R7 is dissolved in 10 grams of water. The R7 solution is introduced into an EFD 780S spray coater. The spray coater can be used to atomize the R7 solution. The atomized R7 solution is then sprayed into a pool of liquid nitrogen. The liquid nitrogen quickly freezes the R7 solution thereby producing R7-water particles. The liquid nitrogen is removed by slowly warming the liquid to about −5° C. The R7-water particles are then washed with acetone to remove the water. The R7 particles are dispersed into a solution of PBMA at a ratio of 1:2 (w/w) R7:PBMA and 1,4-dioxane at a ratio of 2:98 (w/w) of PBMA to 1,4-dioxane. The EFD 780S spray coater can be used to spray the drug-polymer suspension onto a stent.

Example 7

0.5 grams of R7 is dissolved in 10 grams of water. The R7 solution is introduced into an EFD 780S spray coater. The spray coater can be used to atomize the R7 solution. The atomized R7 solution is then sprayed into a pool of liquid nitrogen. The liquid nitrogen quickly freezes the R7 solution thereby producing R7-water particles. The liquid nitrogen is removed by slowly warming the liquid to about −5° C. The R7-water particles are then freeze-dried by feeding the particles into a FreeZone® Freeze Dry System (Labconco Corp., Kansas City, Mo.). The R7 particles are dispersed into a solution of PBMA at a ratio of 1:2 (w/w) R7:PBMA and 1,4-dioxane at a ratio of 2:98 (w/w) of PBMA to 1,4-dioxane. The EFD 780S spray coater can be used to spray the drug-polymer suspension onto a stent.

Example 8

0.5 grams of R7 is dissolved in 10 grams of water. The R7 solution is introduced into a Model BD-200 Bubble Dryer™ (Temco Instruments, Tulsa, Okla.). The dryer produces micronized R7 particles with an average particle size of about 0.65 microns which are then collected and dispersed into a solution of PBMA at a ratio of 1:2 (w/w) R7:PBMA and 1,4-dioxane at a ratio of 2:98 (w/w) of PBMA to 1,4-dioxane. An EFD 780S spray coater can be used to spray the drug-polymer suspension onto a stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent comprising:
   a stent body;
   a coating on a surface of the stent body, the coating comprising a polymer, and;
   an unencapsulated micronized peptide or protein dispersed in the polymer, wherein:
   the peptide or protein comprises from 5 to 1000 L-arginine subunits, or analogs or derivatives thereof.

2. The stent of claim 1, wherein the peptide or protein has an average particle size of less than 2 microns.

3. The stent of claim 1, wherein the solubility profile of the peptide or protein is incompatible with the solubility profile of the polymer.

4. The stent of claim 1, wherein the polymer is a hydrophobic polymer.

5. The stent of claim 1, wherein the peptide is L-heptaarginine, or analogs or derivatives thereof.

6. The stent of claim 1, wherein the polymer comprises a component selected from the group consisting of poly(vinylidene fluoride), poly(butyl methacrylate), poly(isocyanate), poly(ethylene glycol), poly(vinyl pyrrolidone), poly(ethylene-co-vinyl alcohol), poly(2-hydroxyethyl methacrylate), poly(acrylic acid), and combinations thereof.

7. The stent of claim 1, wherein the coating includes an additional active agent for inhibiting migration or proliferation of vascular smooth muscle cells.

8. The stent of claim 7, wherein the active agent comprises a component selected from the group consisting of heparin, heparin sulfate, heparin having a hydrophobic counterion, mannose-6-phosphate, superoxide dismutase, retinoic acid, rapamycin, rapamycin analogs and derivatives, suramin, asiaticoside, hyaluronan and combinations thereof.

9. The stent of claim 1, wherein the peptide or protein includes a component selected from a group consisting of poly(L-arginine), poly(D-arginine), poly(L-lysine), poly(D-lysine), poly(δ-guanidino-α-aminobutyric acid), mixtures of poly(L-arginine) and poly(D-arginine), chitosan, and combinations thereof.

10. The stent of claim 1, wherein the peptide is an oligopeptide or a polypeptide.

11. The stent of claim 1, wherein the peptide or protein includes from 5 to about 20 arginine subunits.

12. The stent of claim 1, wherein the peptide consists of 5 to 20 L-arginine subunits.

13. The stent of claim 1, wherein the polymer is hydrophobic.

14. The stent of claim 1, wherein the peptide or protein is hydrophilic.

15. The stent of claim 1, wherein the peptide or protein is hydrophilic, and the polymer is hydrophobic.

16. A stent, comprising:
   a stent substrate;
   a coating on a surface of the stent substrate, the coating comprising a polymer, and;
   an unencapsulated micronized peptide or protein having an average particle size of less than 2 microns dispersed in the polymer.

17. The stent of claim 16, wherein the peptide or protein includes a component selected from a group consisting of poly(L-arginine), poly(D-arginine), poly(L-lysine), poly(D-lysine), poly(δ-guanidino-α-aminobutyric acid), mixtures of poly(L-arginine) and poly(D-arginine), chitosan, and combinations thereof.

18. The stent of claim 16, wherein the peptide is an oligopeptide or a polypeptide.

19. The stent of claim 16, wherein the peptide or protein includes from 5 to about 20 arginine subunits.

20. The stent of claim 16, wherein the peptide consists of 5 to 20 L-arginine subunits.

21. The stent of claim 16, wherein the peptide is L-heptaarginine, or analogs or derivatives thereof.

22. The stent of claim 16, wherein the polymer is hydrophobic.

23. The stent of claim 16, wherein the peptide or protein is hydrophilic.

24. The stent of claim 16, wherein the peptide or protein is hydrophilic, and the polymer is hydrophobic.

25. An implantable medical device comprising:
   a substrate;
   a coating on the substrate, the coating comprising a hydrophobic polymer, and;
   an unencapsulated micronized polycationic peptide or protein dispersed in the hydrophobic polymer, wherein the micronized polycationic peptide or protein has an average particle size of less than 5 microns.

26. The implantable medical device of claim 25, wherein the device comprises a stent.

27. The implantable medical device of claim 25, wherein the peptide or protein includes components selected from a group consisting of poly(L-arginine), poly(D-arginine), poly(L-lysine), poly(D-lysine), poly(δ-guanidino-α-aminobutyric acid), mixtures of poly(L-arginine) and poly(D-arginine), chitosan, and combinations thereof.

28. The implantable medical device of claim 25, wherein the peptide is L-heptaarginine, or analogs or derivatives thereof.

29. The implantable medical device of claim 25, wherein the peptide consists of 5 to 20 L-arginine subunits.

30. The implantable medical device of claim 25, wherein the peptide includes oligopeptides and polypeptides.

31. The implantable medical device of claim 25, wherein the polymer comprises a component selected from the group consisting of poly(vinylidene fluoride), poly(butyl methacrylate), poly(isocyanate), poly(ethylene glycol), poly(vinyl pyrrolidone), poly(ethylene-co-vinyl alcohol), poly(2-hydroxyethyl methacrylate), poly(acrylic acid), and combinations thereof.

32. The implantable medical device of claim 25, wherein the coating includes an additional active agent.

33. The implantable medical device of claim 25, wherein the active agent comprises a component selected from the group consisting of heparin, heparin sulfate, heparin having a hydrophobic counterion, mannose-6-phosphate, superoxide dismutase, retinoic acid, rapamycin, rapamycin analogs and derivatives, suramin, asiaticoside, hyaluronan, and combinations thereof.

* * * * *

UNITED STATES PATENT AND TRADEMARK OFFICE
CERTIFICATE OF CORRECTION

| | | |
|---|---|---|
| PATENT NO. | : 8,506,617 B1 | Page 1 of 1 |
| APPLICATION NO. | : 10/177942 | |
| DATED | : August 13, 2013 | |
| INVENTOR(S) | : Eugene T. Michal et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2972 days.

Signed and Sealed this
Seventh Day of July, 2015

Michelle K. Lee
*Director of the United States Patent and Trademark Office*